US012055480B2

(12) United States Patent
Reimann et al.

(10) Patent No.: US 12,055,480 B2
(45) Date of Patent: Aug. 6, 2024

(54) METHOD FOR PREDICTING A PROPERTY VALUE OF INTEREST OF A MATERIAL

(71) Applicant: Evonik Operations GmbH, Essen (DE)

(72) Inventors: Ingolf Reimann, Reinheim (DE); Joachim Reising, Kleinostheim (DE)

(73) Assignee: Evonik Operations GmbH, Essen (DE)

( * ) Notice: Subject to any disclaimer, the term of this patent is extended or adjusted under 35 U.S.C. 154(b) by 310 days.

(21) Appl. No.: 17/768,431

(22) PCT Filed: Oct. 5, 2020

(86) PCT No.: PCT/EP2020/077769
§ 371 (c)(1),
(2) Date: Apr. 12, 2022

(87) PCT Pub. No.: WO2021/073908
PCT Pub. Date: Apr. 22, 2021

(65) Prior Publication Data
US 2023/0194415 A1    Jun. 22, 2023

(30) Foreign Application Priority Data

Oct. 17, 2019    (EP) .................................... 19203750

(51) Int. Cl.
| | | |
|---|---|---|
| *G01N 21/27* | (2006.01) | |
| *G01J 3/28* | (2006.01) | |
| *G01N 21/359* | (2014.01) | |
| *G06F 17/16* | (2006.01) | |
| *G06F 18/214* | (2023.01) | |
| *G16C 20/20* | (2019.01) | |
| *G16C 20/30* | (2019.01) | |
| *G16C 60/00* | (2019.01) | |

(52) U.S. Cl.
CPC ......... *G01N 21/274* (2013.01); *G01N 21/359* (2013.01); *G06F 17/16* (2013.01); *G06F 18/214* (2023.01); *G16C 20/20* (2019.02); *G16C 20/30* (2019.02); *G16C 60/00* (2019.02); *G01J 2003/2866* (2013.01); *G01N 2201/129* (2013.01)

(58) Field of Classification Search
CPC .......... G01J 2003/2866; G01N 21/274; G01N 21/359; G01N 2201/129; G06F 17/16; G06F 18/214; G16C 20/20; G16C 20/30; G16C 60/00
See application file for complete search history.

(56) References Cited

U.S. PATENT DOCUMENTS

| | | | | |
|---|---|---|---|---|
| 5,121,337 A | * | 6/1992 | Brown ............... | G01N 21/3504 702/28 |
| 5,360,972 A | * | 11/1994 | DiFoggio ........... | G01N 21/3577 702/30 |
| 5,446,681 A | * | 8/1995 | Gethner ............... | G01R 35/005 703/2 |
| 5,568,400 A | * | 10/1996 | Stark ........................ | G01J 3/28 702/191 |
| 5,606,164 A | | 2/1997 | Price et al. | |
| 5,668,374 A | * | 9/1997 | DiFoggio ........... | G01N 33/2829 702/30 |
| 5,945,675 A | * | 8/1999 | Malins ..................... | G01J 3/45 250/339.08 |
| 6,549,861 B1 | * | 4/2003 | Mark ........................ | G01J 3/28 73/659 |
| 6,584,413 B1 | * | 6/2003 | Keenan .................... | G01J 3/28 702/194 |
| 6,587,575 B1 | * | 7/2003 | Windham ............... | A22B 5/007 382/110 |
| 6,629,041 B1 | * | 9/2003 | Marbach ............... | G01N 21/359 250/252.1 |
| 6,675,106 B1 | * | 1/2004 | Keenan .................... | G01J 3/28 702/194 |
| 6,754,543 B1 | * | 6/2004 | Wold .................. | G01N 21/359 700/52 |
| 6,793,624 B2 | * | 9/2004 | Tsenkova ............. | G01N 21/359 119/14.14 |
| 6,871,169 B1 | * | 3/2005 | Hazen ................. | G01N 21/359 703/2 |
| 2001/0000150 A1 | * | 4/2001 | Malins .................... | G01J 3/453 435/6.14 |

(Continued)

OTHER PUBLICATIONS

International Search Report and Written Opinion mailed on Jan. 11, 2021 in PCT/EP2020/077769 filed on Oct. 5, 2020, 19 pages.
R. De Maesschalck et al., "Tutorial the Mahalanobis distance", Chemometrics and Intelligent Laboratory Systems, vol. 50, 2000, pp. 1-18, XP004184173.
Charles E. Miller et al., "The use of chemometric techniques in process analytical method development and operation", Chemometrics and Intelligent Laboratory Systems, vol. 30, 1995, pp. 11-22, XP004037874.
European Search Report mailed Mar. 27, 2020, in EP 19203750.5 filed on Oct. 17, 2019, 6 Pages.
U.S. Appl. No. 15/431,597, filed Feb. 13, 2017, Markus Wiltafsky et al.
U.S. Appl. No. 16/485,054, filed Aug. 9, 2019, 2019/0360986 A1, Markus Wiltafsky et al.

(Continued)

*Primary Examiner* — Blake C Riddick
(74) *Attorney, Agent, or Firm* — Oblon, McClelland, Maier & Neustadt, L.L.P.

(57) ABSTRACT

The present invention relates to a computer-implemented method for predicting a property value of interest in a sample investigated by infrared spectroscopy. The method aims at generating a calibration function. To this end, a set of calibration samples is selected, whereby outliers are identified and removed from the set of calibration samples. Outliers are determined using principal component analysis and singular value decomposition. The threshold value separating outliers from the remaining samples is calculated on the basis of a predetermined formulae. The threshold value may also be increased stepwise in order to dynamically set the threshold value, which is preferable for spectroscopic devices not operated under laboratory conditions.

15 Claims, No Drawings

(56) References Cited

U.S. PATENT DOCUMENTS

| | | | | |
|---|---|---|---|---|
| 2003/0048432 A1* | 3/2003 | Jeng | G01N 21/4133 | 356/326 |
| 2003/0087456 A1* | 5/2003 | Jones | A61B 5/7264 | 436/171 |
| 2003/0162301 A1* | 8/2003 | Noergaard | A61B 5/7267 | 422/52 |
| 2003/0200040 A1* | 10/2003 | Trygg | G01N 21/359 | 702/85 |
| 2004/0064259 A1* | 4/2004 | Haaland | G01N 21/274 | 702/18 |
| 2004/0064299 A1* | 4/2004 | Mark | G01N 21/274 | 703/13 |
| 2004/0111220 A1* | 6/2004 | Ochs | G06F 18/2134 | 702/19 |
| 2004/0142402 A1* | 7/2004 | Maruo | A61B 5/7264 | 435/14 |
| 2004/0142496 A1* | 7/2004 | Nicholson | A61B 5/412 | 436/536 |
| 2004/0214348 A1* | 10/2004 | Nicholson | A61B 5/7264 | 436/518 |
| 2005/0037515 A1* | 2/2005 | Nicholson | G01R 33/465 | 436/173 |
| 2005/0149300 A1* | 7/2005 | Ruchti | G01N 21/359 | 703/2 |
| 2006/0197956 A1* | 9/2006 | Jones | G01J 3/28 | 356/454 |
| 2006/0197957 A1* | 9/2006 | Jones | G01N 21/274 | 356/454 |
| 2007/0043518 A1* | 2/2007 | Nicholson | G16B 20/20 | 702/23 |
| 2007/0184455 A1* | 8/2007 | Arrowsmith | G01R 33/465 | 435/6.12 |
| 2008/0112853 A1* | 5/2008 | Hall | G01N 21/3577 | 422/68.1 |
| 2008/0319712 A1* | 12/2008 | Claps | G01N 21/359 | 702/189 |
| 2009/0192721 A1* | 7/2009 | Clayton | G01N 33/5038 | 703/11 |
| 2011/0184683 A1* | 7/2011 | Soller | G01N 21/3577 | 702/85 |
| 2011/0216313 A1* | 9/2011 | Li | G01N 33/15 | 356/301 |
| 2013/0080070 A1* | 3/2013 | Pai | G16C 20/70 | 702/19 |
| 2014/0353503 A1* | 12/2014 | Lanan | G01N 24/087 | 250/339.01 |
| 2016/0153899 A1* | 6/2016 | Lambert | G01N 21/359 | 250/339.07 |
| 2019/0049297 A1* | 2/2019 | Luan | G01J 3/0275 | |
| 2019/0178794 A1* | 6/2019 | Klapproth | G01N 21/3577 | |
| 2020/0178808 A1* | 6/2020 | Asano | A61B 5/7257 | |

OTHER PUBLICATIONS

U.S. Appl. No. 17/311,911, filed Jun. 8, 2021, 2022/0026350 A1, Ingolf Reimann et al.

U.S. Appl. No. 17/621,964, filed Dec. 22, 2021, Ingolf Reimann et al.

U.S. Appl. No. 17/622,140, filed Dec. 22, 2021, Ingolf Reimann et al.

* cited by examiner

METHOD FOR PREDICTING A PROPERTY VALUE OF INTEREST OF A MATERIAL

The present invention relates to a computer-implemented method for predicting a property value of interest of a material and a device for this method comprising a processing unit adapted to carry out said method.

Near infrared (NIR) spectroscopy is a useful tool for predicting a property value of interest of a material, in particular when far away from an analytical laboratory where the analysis, qualitative and/or quantitative, would normally be performed. In particular, agricultural products, such as feedstuff raw materials and/or feedstuffs, may be analyzed for the presence and concentration of specific ingredients prior to and after proceeding stages such as toasting and pressure treatments, during or after storing and after preparation of the feed containing them. However, it needs an adequate calibration function in order to provide precise and reliable predictions by means of near infrared spectroscopy.

Said calibration function is typically generated by means of multivariate analysis. This allows for a proper consideration of correlations for estimating the composition of complex mixtures with a compensation for interferences from background signals. A prediction of a property value of interest by means of NIR spectroscopy and a calibration function represents a two-step process. In the first step, a calibration model is constructed by utilizing a dataset obtained by indirect measurements, for example of optical signal intensity, and direct measurements, for example of the concentration of analytes, in a number of situations spanning a variety of different analyte and instrumental conditions. A general form for the relationship between direct (e.g. concentration of the analyte) and indirect (e.g. optical signal intensity) measurements is $y=f(x_1, x_2, \ldots, x_n)$, where y is the desired property value of interest to be predicted (e.g. concentration of the analyte), $f$ is some function (model), and $x_1, x_2, \ldots, x_n$ are the arguments of the model, and specifically the results of any indirect measurements, for example transformed optical measurements at a (specific) number of wavelengths. The goal of this first step is to develop a useful function $f$ which reflects the relationship between the indirect measurement(s) and the desired property value of interest to be predicted. In the second step (prediction), this function is evaluated with a measured set of indirect (optical) measurements $x_1, x_2, \ldots, x_n$ in order to obtain an estimate of the direct measurement (e.g. concentration of the analyte) at some time in the future when optical measurements are to be made without a corresponding direct measurement.

There is a vast number of literature regarding the creation of a calibration function for making predictions of a property value of interest of a material by means of NIR spectroscopy. Most of the prior art relates to the general and specific concepts for creating a calibration function. Some literature is dedicated to the compensation of interferences, e.g. environmental interferences and device-specific errors such as measurement errors and ageing emission sources, in the creation of the calibration function. The prior art, however, does not consider the identification of spectral outliers, let alone how to deal with them in the creation of the calibration function but, it is very likely that they will occur during the accumulation of indirect (optical) measurements. As a consequence thereof, it is also very likely that they will impair the creation of the calibration function. An outlier may be due to variability in the measurement or it may be the result of an instrumental error; the latter are sometimes excluded from the data set. In general, and in particular in statistics, an outlier is considered a data point that differs significantly from other observations, which however leaves much space for subjective interpretation and misinterpretation. On the other hand, the inclusion of data points at the fringes of a data set is necessary for a meaningful and robust calibration and therefore, should not be simply skipped just because they appear to be odd. This already shows that one, if not the major problem associated with outliers is their detection or identification because there is not rigid definition of an outlier. Ultimately, it is therefore still a subjective exercise to determine if an observation is an outlier or not. Due to the lack of a generally accepted definition of an outlier, there are various methods for detecting an outlier. Some are graphical such as normal probability plots, others are model-based, and hybrid methods such as so-called box plots. And the choice of the method and how to deal with an outlier often depends on the individual case. Even when a normal distribution model is appropriate to the data being analyzed, outliers must be expected for large sample sizes and should not automatically be discarded when they are present. The respective application should use a classification algorithm that is robust to outliers to model data with naturally occurring outliers. Deletion of outlier data is a controversial practice frowned upon by many scientists and science instructors. It is more acceptable in the areas of practice, where the underlying model of the process and the usual distribution of measurement errors is confidently known. An outlier resulting from an instrumental reading error may be excluded but it is desirable that the reading is at least verified. In particular, in the case of infrared spectroscopy, it is a big challenge to identify outliers as accurately as possible and also very efficiently, at best both at the same. This is even more relevant when the respective infrared spectra (indirect measurements) and the corresponding reference data (direct measurements) shall be the basis for the creation of a calibration function that is suitable for predicting a property value of interest of a material by means of infrared spectroscopy.

Thus, there was a need for a method for predicting a property value of interest of a material by means of infrared spectroscopy, which allows for the reliable and automatic identification and removal of spectral outliers during the creation of the calibration function.

Object of the present invention is therefore a computer-implemented method for predicting a property value of interest of a material, comprising the steps of a) providing a population of infrared spectra of samples, wherein said spectra form an m×n input data matrix X, with m being the number of samples in rows and n being the data points in columns, b) removing spectral outliers from the spectra population of step a), comprising the steps of b1) obtaining the principal components by subjecting the matrix X to a principal component analysis, b2) producing a diagonal matrix $\Sigma$, containing singular values $\sigma_m$ of the matrix X, and a loadings matrix V, from the input data matrix X, b3) calculating a score $x_m$ for each spectrum by multiplying each data point of the input data matrix X with the loadings for each component of step b2), forming the mean of each column of the X-matrix to provide $B_{0,m}$ values, and calculating a scoring index si by the formula $$si = \sum_i \frac{(x_m - B_{0,m})}{\sigma_m}$$

b4) determining the number of components $N_C$ whose eigenvalues lead to a convergence in the regression of X on the scores of at least 99%, and calculating a distance measure threshold value $D_i$ for every spectrum of step a), by the formula $$D_i = N_C \times \sqrt[2]{\frac{(si^2 \times N_C)}{(N_C - 1)}}$$

b5) calculating the mean for all scores of each principal component of each spectrum of step a) and calculating the distance measure between said mean and each of the scores of each principal component,
b6) considering a sample spectrum as a spectral outlier when the value of the distance measure for a score of a principle component obtained in step b5) is larger than the distance measure threshold value of step b4),
b7) removing the spectral outlier of step b6) from the spectra population of step a) to give a cleaned spectra population,
c) generating a prediction function on the cleaned spectra population of step b7),
d) providing an infrared spectrum of a sample of unknown origin and/or composition or of the same origin and/or composition as a sample in step a), and
e) predicting a property value of interest from the spectrum of step d) by means of the prediction function of step c).

The population of infrared spectra of samples provided in step a) defines an n-dimensional data space, where n is the number of data points in the spectra and m is the number of samples. Therefore, the data of the infrared spectra can be represented by an input data matrix of the type $X_{m \times n}$ with m rows for the samples and n columns for the data points, often also written as m×n matrix X. The sheer amount of data makes the resulting matrix rather complex. Hence, the input data matrix is subjected to a data reduction, without losing relevant information. This is typically done in a principal component analysis (PCA). This is a statistical procedure that uses an orthogonal transformation to convert a set of observations of possibly correlated variables (entities each of which takes on various numerical values) into a set of values of linearly uncorrelated variables called principle components. This transformation is defined in such a way that the first principal component has the largest possible variance, i.e. it leads to the highest possible variability in the data. Each further component is orthogonal to the preceding component(s) and is second to the preceding component in terms of the highest possible variance. The resulting vectors (each being a linear combination of the variables and containing n observations) are an uncorrelated orthogonal basis set. In a principal component analysis, the input data matrix $X_{m \times n}$ is decomposed into two matrices which are orthogonal to each other, the $U_{m \times n}$ matrix and the $V_{n \times n}^T$ matrix. Mathematically, this step is described by the formula $$X_{m \times n} = U_{m \times n} \times V_{n \times n}^T$$

$V_{n \times n}^T$ is the so-called loadings-matrix, which contains the loadings, i.e. the new axes resulting from the transformation, and $U_{m \times n}$ is also called the so-called scores-matrix, which contains the new coordinates. The loadings can be understood as the weights by which the original variables are to be multiplied in order to calculate the principal components.

According to present invention the input data matrix X is decomposed into a product of several matrices by means of a singular value decomposition, which is mathematically described by $$X_{m \times n} = U_{m \times n} \times \Sigma_{m \times n} \times V_{n \times n}^*$$

where $X_{m \times n}$ is an m×n matrix of the rank k, $U_{m \times m}$ is a unitary m×m matrix, $\Sigma_{m \times n}$ is a real m×n matrix containing the singular values $\sigma_m$ of the matrix X, and $V_{n \times n}^*$ is the adjoint of the unitary n×n matrix V containing the loadings; with real numbers the adjoint matrix is equivalent to the transposed matrix $V_{n \times n}^T$.

In the context of the present invention a population of infrared spectra is not subject to any limitation regarding the number of spectra, provided that the number of spectra is sufficient to generate a meaningful prediction function. Hence, the number of spectra in a population of spectra can range from 50 to 10,000, from 50 to 5,000, from 50 to 2,500, from 50 to 2,000, from 50 to 1,500, from 50 to 1,000, from 100 to 1,000, from 50 to 500, from 100 to 500, from 50 to 250, from 100 to 250, or from 50 to 100.

The infrared spectrum/spectra can be recorded at wavelengths between 400 and 2,800 nm with any suitable spectrometers working either on the monochromator principle or on the Fourier transform principle. Preferably, an infrared spectrum is recorded between 1,100 and 2,500 nm. Wavelengths are easily convertible into the respective wavenumbers and therefore, an infrared spectrum can also be recorded at the corresponding wavenumbers. In general, infrared spectroscopy requires the presence of functional groups or moieties, which permit for excitation of molecular vibration in the material by irradiation, and the frequency of the light coming through is then recorded by the spectrometer. However, it is also possible to record infrared spectra of a material that does not have any functional groups or moieties, for example minerals, which taken alone do not permit for any (molecular) vibrations. This, however, requires the simultaneous presence of an infrared active material, which interacts with the non-infrared active material, for example in the formation of a complex compound, and thus, is subject to vibrational changes in the excitation of the molecular vibrations. The comparison of the thus obtained infrared spectrum with a spectrum of the (pure) infrared active material in the absence of the additional infrared inactive material, allows to draw conclusions on the identity and concentration of the infrared inactive material. Accordingly, infrared spectroscopy permits the prediction of a property value of interest of a broad variety of different materials. However, a biological sample such as a feedstuff contains a multitude of different organic and inorganic compounds and thus represents a rather complex matrix. Notwithstanding, every biological substance gives a unique near-infrared spectrum, comparable to an individual fingerprint. Consequently, two biological substances giving identical spectra can be assumed to have the same physical and chemical composition and thus to be identical. On the other hand, if two biological substances give different spectra, it can be assumed that they are different, either in terms of their physical or chemical characteristics, or in both terms. Due to their individual and highly specific absorption bands the signals of organic and inorganic compounds and their intensities in infrared spectra can be easily attributed and correlated to a specific organic compound and its concentration in a sample of known weight. Thus, infrared spectroscopy permits the prediction of a property value of interest of a rather complex material, such as the identity and concentration of different amino acids and proteins in a biological sample. However, infrared spectrum also permits to identify even an abstract parameter in complex samples, when it is possible to identify general trends in the same type of sample due to the changes of said abstract parameters. For example, it is possible to attribute and correlate absorptions and their intensities in an infrared spectrum of the complex sample of a feedstuff or feedstuff raw material to abstract parameters, such as the trypsin inhibitor activity, urease activity, protein solubility in alkali and protein dispersibility index, and their concentrations. In the next step, the involved infrared spectrometer must be calibrated. Once, the absorption intensities at the respective wavelengths or wavenumbers have been successfully matched, i.e. attributed and correlated to the parameters of interest and their values, the near infrared spectroscopy allows for a reliable prediction of a property value of interest of a material. For this purpose, a sufficient number of infrared spectra, if necessary 100, 200, 300, 400, 500 or more, of the material in question are recorded, and the absorption intensities at the respective wavelengths or wavenumbers are matched with the corresponding parameters and their values. An infrared spectrum can be measured in transmission or reflectance mode. In academic use the most common measurement mode is the transmission mode but for the measurement of insoluble or grainy materials it is preferred to measure in reflectance mode. In the latter case, the reflectance of the light coming back from the sample is measured and the difference between the emitted and the reflected light is given as absorption.

In general, the method according to the present invention is not subject to any limitations regarding the material whose property value of interest is to be predicted. Hence, it can a singular substance or a mixture of different substances. As explained above in more detail, the material must contain at least one infrared active substance to allow for the excitation of molecular vibration(s). Apart form that, the material can be of any type of composition and/or origin. Suitable materials in context of the present invention are organic compounds, such as amino acids, peptides, proteins, carboxylic acids, fatty acids, saturated and/or unsaturated fatty acids, polyunsaturated fatty acids, or mixtures thereof, or materials of human, animal or vegetable origin, for example digesta, body parts, animal parts or plant parts, or technically produced products based upon plant and/or animal originating products, e.g. feedstuffs, animal diets and/or feedstuff raw materials, such as distillers grains with solubles (DDGS), hydrolyzed fish meal or hydrolyzed feather meal, and inorganic compounds, such as carbonates, phosphates, nitrates, and sulfates, or a mixture thereof. Preferably, the material whose property value of interest is to be predicted is an amino acid, a protein, a peptide, a carboxylic acid, a saturated, unsaturated and/or partially saturated fatty acid, a polyunsaturated fatty acid, a feed, a feedstuff, a feedstuff raw material, a substance of human, animal and/or vegetable origin or a mixture thereof.

The material which is subjected to the method according to the present invention strongly influences the property value of interest to be predicted. For example, when a feed, a feedstuff, or a feedstuff raw material is the material subjected to the method according to the present invention, then a property value of interest to be predicted is in particular an amino acid, a polyunsaturated fatty acid, and/or a mineral nutrient. For example, when digesta, body parts, or animal parts are the material subjected to the method according to the present invention, then a property value of interest to be predicted is in particular a protein, a peptide, and/or an amino acid. Hence, the method according to the present invention is in principle not subject to any limitations regarding the property value of interest to be predicted. Therefore, the property value of interest can be any type of parameter of a material, which can be determined either directly or indirectly by means of infrared spectroscopy.

According to the present invention the sample whose infrared spectrum is provided in step d) is a sample of unknown origin and/or composition or of the same origin and/or composition as a sample in step a). Preferably, the sample in step d) is of unknown origin and/or composition. Alternatively, it is preferred that the sample in step d) is of the same origin as a sample in step a) but of unknown composition. Preferably, the sample whose infrared spectrum is provided in step d) is a sample of unknown origin and/or composition or of the same origin and/or composition as the population of samples in step a). Preferably, the sample in step d) is of unknown origin and/or composition. Alternatively, it is preferred that the sample in step d) is of the same origin as the population of samples in step a) but of unknown composition.

Since infrared spectra can be measured in transmission or reflectance mode, the sample can be an unground and/or ground sample, wherein the ground sample can be of different granularity.

In principle, the method according to the present invention is not subject to any limitations regarding the use of the distance measure. Therefore, any suitable distance measure can in principle be used in the method, e.g. the Euclidian distance measure, the Pearson distance measure, or the Mahalanobis distance measure. In general, it is possible to define a distance measure, given as distance coefficient d(i,j) of two observations i and j, from a similarity measure s(i,j) of two observations i and j, by means of the formula $$d(i,j) = \sqrt{s(i,i) + s(j,j) - 2s(i,j)}$$

Therefore, it is also possible to obtain the distance measure indirectly, i.e. first the similarity measure is determined, followed by obtaining the distance measure from the similarity measure.

In an embodiment of the method according to the present invention the distance measure is the Euclidian distance measure, the Pearson distance measure, the Mahalanobis distance measure, or a distance measure obtained from a similarity measure.

Typically, any type of similarity analysis works with a threshold value that defines some kind of limit, which observations are still acceptable and which are no longer acceptable. The use of strict threshold values for a distance or similarity measure typically may work fine under laboratory and thus very reproducible conditions, with well trained staff and spectrometers, which are ideally calibrated and part of a network. However, the use of strict threshold values for a distance or similarity measure does not work fine, when so-called standalone spectrometers are used, which are typically not operated under laboratory conditions. Further, the choice of a strict threshold value for a distance measure would again be a rather subjective thing, in particular if said threshold value was only randomly selected or adopted from other procedures. It is therefore rather likely, that the use of strict pre-defined threshold values for a distance or similarity measure would lead to similar problems as in the prior art. However, the method according to the present invention shall also be suitable for predicting property values of interest using so-called stand-alone spectrometers, which are typically not operated under laboratory conditions.

In the context of the present invention it was found that these problems are solved by use of a so-called dynamic threshold value for the distance measure. This approach of a dynamic threshold value involves a stepwise increase of the distance measure threshold value obtained in step b4) by +1. The thus obtained "new" distance measure threshold value serves as a basis for assessing whether a sample spectrum is a spectral outlier, here the distance measure threshold value obtained in step b4) is replaced by the "new" distance measure threshold value. This procedure is repeated until the difference between the two distance measures with the highest values is at least 1 and the highest value of a distance is 8 at the most.

In another embodiment of the method according to the present invention the step b) further comprises the steps of
  b5.1) increasing the distance measure threshold value obtained in step b4) by +1,
  b5.2) determining the two distance measures obtained in step b5) with the highest values using the distance measure threshold value of step b5.1),
  b5.3) determining the difference between the values of the distance measures determined in step b5.2), and
  b5.4) repeating the steps b5.1) to b5.3) with the distance measure threshold value of step b5.1) until the difference determined in step b5.3) is at least 1, and the highest value of a distance measure is 8 at the most.

Each time the steps b5.1) to b5.3) are repeated, the distance measure threshold value from the last run replaces the distance measure threshold value from the preceding run, i.e. the run before the last run, and is then increased by +1 in the repeated step b5.1). Hence, when the steps b5.1) to b5.3) are repeated for the first time, the distance measure threshold value obtained in step b4) is replaced by the distance measure threshold value obtained in step b5.1) and this distance measure threshold value is then increased by +1 in the repeated step b5.1). When the steps b5.1) to b5.3) are repeated yet again, the distance measure threshold value from the last run replaces the distance measure threshold value from the second to last run in the repeated step b5.1) and the distance measure threshold value from the last run is then increased by +1 in the repeated step b5.1).

Preferably, the generation of the prediction function on the cleaned spectra population of step b7) involves the use of a set of reference data, obtained from the determination of the property value of interest in each sample of step a) in a quantitative analysis.

In another embodiment the method according to the present invention further comprises the step
  a1) determining the property values of interest in each sample of step a) in a quantitative analysis to give a set of reference data.

In the context of the present invention the term quantitative analysis is used in its broadest sense known to the person skilled in the art, preferably in the art of analytical chemistry, and denotes any chemical and/or physical method for the determination of the absolute or relative presence of one, several or all particular parameters, for example the presence of specific substance(s), in a sample. For example, when the sample in question is from a feed, feedstuff or feedstuff raw material, the particular parameter can be the absolute or relative presence of one, several or all of the amino acids from the list consisting of methionine, cysteine, cystine, threonine, leucine, arginine, isoleucine, valine, histidine, phenylalanine, tyrosine, tryptophan, glycine, serine, proline, alanine, aspartic acid, glutamic acid, the total amount of lysine, the reactive amount of lysine and the ratio of the reactive amount of lysine to the total amount of lysine. The term the reactive amount of lysine is used to denote the amount of lysine, which is actually available for the animal, in particular for the digestion in the animal. By comparison, the term the total amount of lysine is used to denote the sum of the amount of lysine, which is actually available for the animal, in particular for the digestion in the animal, and of the amount of lysine, which is not available for the animal, in particular not for the digestion in the animal. The latter amount of lysine is typically due to degradation reactions of lysine, such as the already mentioned Maillard reaction.

Many feedstuffs are processed which leads to possible damages to the amino acids. This may render some of the amino acids unavailable for their use in nutrition. This is particularly the case for lysine, which has an ε-amino group that can react with the carbonyl group of other compounds, e.g. reducing sugars, present in the diet to give compounds that may be partially absorbed from the gut but which do not have any nutritional value to the animal. The reaction of the ε-amino group of free and/or protein-bound lysine with reducing sugars during heat treatment is known as the Maillard reaction. This reaction gives both early and late Maillard products. The early Maillard products are structurally altered lysine derivatives that are called Amadori compounds, while the late Maillard products are called melanoidins. The melanoidins do not interfere with the normal analysis for lysine and have no influence on the digestibility values that are calculated. They only result in lower concentrations of lysine being absorbed. Therefore, the melanoidins are typically not identified in the regular analysis of amino acid. By comparison, the Amadori compounds do interfere with the amino acid analysis and give inaccurate lysine concentrations for the sample being analyzed. The lysine being bound in these compounds is called "blocked lysine" and is biologically unavailable because it is resistant to any gastrointestinal enzymatic degradation.

The reactive lysine content in a sample can be determined using the Sanger reagent, i.e. 1-fluoro-2,4-dinitrobenzene (FNDB). The lysine determined by means of this method is therefore also referred to as FDNB-lysine. The Sanger reagent converts lysine to the yellow dinitrophenyl (DNP)-lysine, which can be extracted and measured spectrophotometrically at a wavelength of 435 nm or by high-performance liquid chromatography.

Alternatively, the reactive lysine content in a sample can be also determined with the guanidination reaction using the mild reagent O-methylisourea. In this method the O-methylisourea only reacts with the ε-amino group of lysine, but it does not react with the α-amino group of lysine. Therefore, the guanidination reaction can be used to determine free lysine and peptide-bound lysine. Preference is therefore given for the guanidation reaction for the determination of the reactive lysine. The guanidination reaction of lysine gives a homoarginine, which is further derivatized with ninhydrin and the resulting change in absorption can be measured at wavelength of 570 nm. Subsequently, the derivatized sample is hydrolyzed to give again the homoarginine. The determination of reactive lysine can also be done by means of the guanidation reaction of the undamaged protein-bound lysine in an alkaline medium to give homoarginine. In this type of reaction the guanidation is typically effected through the action of O-methylisourea (OMIU).

Since it is an easier method to use, preference is given to use the guanidination reaction for the determination of reactive lysine. The guanidation reaction involves the incubation of a sample of a feedstuff raw material or feedstuff in O-methylisourea. Preferably, the ratio of O-methylisourea to lysine is greater than 1000. The thus treated sample obtained from step i) is dried and analyzed for homoarginine, preferably by using ion exchange high performance liquid chromatography. Subsequently, said sample is derivatized with ninhydrin and the absorbance of the derivatized sample is measured at a wavelength of 570 nm. Afterwards, said sample is subjected to a hydrolysis. The weight and the molar quantity of homoarginine in the sample are determined. Finally, the amount of reactive lysine is calculated from the molar quantity of homoarginine.

However, not only lysine is subject to heat damages in the processing of feedstuff raw materials and/or feedstuffs but also other amino acids. According to the method of the present invention, the amino acids methionine, cysteine, cystine, threonine, leucine, arginine, isoleucine, valine, histidine, phenylalanine, tyrosine, tryptophan, glycine, serine, proline, alanine, aspartic acid and glutamic acid are quantitatively analyzed in a sample of a feedstuff raw material and/or feedstuff. To a certain degree, amino acids are not only present as single compounds but also as oligopeptides, e.g. dipeptides, tripeptide or higher peptides, formed in an equilibrium reaction from two, three or even more amino acids. The amino group of an amino acid is usually too weak as a nucleophile to react directly with the carboxyl group of another amino acid or it is present in protonated form ($-NH_3^+$). Therefore, the equilibrium of this reaction is usually on the left side under standard conditions. Notwithstanding, depending on the individual amino acids and the condition of a sample solution some of the amino acid to be determined may be not present as single compounds but to a certain degree as oligopeptides, e.g. dipeptide, tripeptide or higher peptide, formed of two, three or even more amino acids. Therefore, the sample of a feedstuff raw material and/or feedstuff should be subjected to a hydrolysis treatment, preferably an acidic or a basic hydrolysis, using for example hydrochloric acid or barium hydroxide. In order to facilitate the separation of the free amino acids and/or the identification and determination of the amino acids, the free amino acids are derivatized with a chromogenic reagent, if necessary. Suitable chromogenic reagents are known to the person skilled in the art. Subsequently, the free amino acids or the derivatized free amino acids are subjected to a chromatographic separation, in which the different amino acids are separated from each other because of the different retention times due to the different functional groups of the individual amino acids. Suitable chromatography columns, for example ion exchange columns or reversed phase columns, and suitable eluent solvent for the chromatographic separation of amino acids are known to the person skilled in the art. The separated amino acids are finally determined in the eluates from the chromatography step by comparison with a calibrated standard, prepared to the analysis. Typically, the amino acids, which are eluted from the chromatography column, are detected with a suitable detector, for example with a conductivity detector, a mass-specific detector or a fluorescence detector or a UV/VIS-detector depending when the amino acids were derivatized with a chromogenic reagent. This gives a chromatogram with peak areas and peak heights for the individual amino acids. The determination of the individual amino acids is performed by comparing the peak areas and peak heights with a calibrated standard or calibration curve for each amino acid. Since cystine ($HO_2C(-H_2N)CH-CH_2-S-S-CH_2-CH(NH_2)-CO_2H$) and cysteine ($HS-CH_2-CH(NH_2)-CO_2H$) are both determined as cysteic acid ($HO_3S-CH_2-CH(NH_2)-CO_2H$) after acidic hydrolysis, the quantitative analysis does not make any distinction between the two amino acids due to the fact that cysteine is very susceptible for oxidation.

The procedure described above is in general used for the quantitative analysis of the total amount of lysine, which is required for the determination of the ratio of the reactive amount of lysine to the total amount of lysine, and for the quantitative analysis of at least one amino acid selected from the group consisting of methionine, cysteine, cystine, threonine, leucine, arginine, isoleucine, valine, histidine, phenylalanine, tyrosine, tryptophan, glycine, serine, proline, alanine, aspartic acid and glutamic acid.

The most critical point in the quantitative analysis of amino acids is the sample preparation, which differs with respect to the type of ingredients and the amino acids of major interests. Most of the amino acids can be hydrolyzed by a hydrolysis in hydrochloric acid (6 mol/l) for a duration of up to 24 hours. For the sulfur containing amino acids methionine, cysteine, and cystine the hydrolysis is preceded by an oxidation, preferably with performic acid. For the quantitative analysis of tryptophan the hydrolysis is performed with barium hydroxide (1.5 mol/l) for 20 hours.

When the sample in question is from a feed, feedstuff or feedstuff raw material, the particular parameter can also be one, several or all from the list consisting of trypsin inhibitor activity, urease activity, protein solubility in alkali and protein dispersibility index of the sample.

The quantitative analysis of the trypsin inhibitor activity is based on the ability of the inhibitors to form a complex with the enzyme trypsin and thus reduce its activity. Trypsin catalyzes the hydrolysis of the synthetic substrates N-alpha-benzoyl-D,L-arginine-p-nitroanilide (DL-BAPNA, IUPAC name N-[5-(diaminomethylideneamino)-1-(4-nitroanilino)-1-oxopentan-2-yl]benzylamide) and N-alpha-benzoyl-L-arginine-p-nitroanilide (L-BAPNA, IUPAC name N-[5-(diaminomethylideneamino)-1-(4-nitroanilino)-1-oxopentan-2-yl]benzylamide). This catalyzed hydrolysis releases the yellow-colored product p-nitroaniline free and thus, leads to a change in absorbance. The trypsin activity is proportional to the yellow color. The concentration of the p-nitroaniline can be determined by means of spectroscopy at a wavelength of 410 nm. L-BAPNA is typically used in the method ISO 14902 (2001) und DL-BAPNA is typically used in the method AACC 22.40-01 (a modification of method originally invented by Hamerstrand in 1981).

In the method ISO 14902 the sample is first finely ground with a 0.50 mm sieve. During the grinding any evolution of heat should be avoided. The ground sample is mixed with aqueous alkaline solution, e.g. 1 g of sample in 50 ml of sodium hydroxide solution (0.01 N), and the thus obtained solution, suspension, dispersion or emulsion is then stored for a period of up to ca. 24 hours at a temperature of 4° C. at the most. The thus obtained mixture has a pH of from 9 to 10, especially of from 9.4 to 9.6. The resulting solution is diluted with water and left standing. A sample of this solution, e.g. 1 ml, is taken and diluted as indicated by its presumed or previously approximated trypsin inhibitor activity content so that 1 ml of diluted solution would cause a 40 to 60% inhibition of the enzymatic reaction. Trypsin working solution, e.g. 1 ml, is added to a mixture of L-BAPNA, water and the diluted sample extract solution, e.g. 5 ml of L-BAPNA, 2 ml of (distilled) water and 1 ml of the appropriately diluted sample extract solution. The samples are then incubated for exactly 10 minutes at 37° C. The reaction is stopped by addition of 1 ml of acetic acid (30%). A blank sample is prepared as above, but the trypsin is added after the acetic acid. After centrifugation at 2.5 g, the absorbance is measured at a wavelength of 410 nm.

In the method AACC 22-40.01 the sample is first finely ground with a 0.15 mm sieve. During the grinding any evolution of heat should be avoided. The ground sample is mixed with aqueous alkaline solution, e.g. 1 g of sample in 50 ml of sodium hydroxide solution (0.01 N), and slowly stirred for 3 hours at 20° C. The pH of the thus obtained solution, suspension, dispersion or emulsion should be between 8 and 11, preferably between 8.4 and 10. The resulting solution, suspension, dispersion or emulsion is diluted with water, shaken and left standing. A sample of this solution, e.g. 1 ml, is taken and diluted as indicated by its presumed or previously approximated trypsin inhibitor activity content so that 1 ml of diluted solution would cause a 40 to 60% inhibition of the enzymatic reaction. Trypsin working solution, e.g. 2 ml, is added to a mixture of D,L-BAPNA, water and the diluted sample extract solution, e.g. 5 ml of D,L-BAPNA, 1 ml of (distilled) water and 1 ml of the appropriately diluted sample extract solution. The samples are then incubated for exactly 10 minutes at 37° C. The reaction is stopped by addition of 1 ml of acetic acid (30%). A blank sample is prepared as above, but the trypsin is added after the acetic acid. After centrifugation at 2.5 g, the absorbance is measured at a wavelength of 410 nm.

Independently from the method used, the trypsin inhibitor activity is calculated as mg trypsin inhibitor per g trypsin, with the following formula:

$$i = \frac{(Ar - Abr) - (As - Abs)}{(Ar - Abr)}$$

i=inhibition percentage (%);
Ar=absorbance of the solution with standard;
Abr=absorbance of the blank with standard;
As=absorbance of the solution with sample;
Abs=absorbance of the blank with sample;

$$TIA = \frac{i}{100} = \times \frac{m1 \times f1 \times f2}{m0}$$

TIA=trypsin inhibitor activity (mg/g);
i=inhibition percentage (%);
m0=mass of the test sample (g);
m1=mass of trypsin (g);
f1=dilution factor of the sample extract; and
f2=conversion factor based on the purity of trypsin.

One trypsin unit is defined as the amount of enzyme, which will increase the absorbance at 410 nm by 0.01 unit after 10 minutes of reaction for each 1 ml of reaction volume. Trypsin inhibitor activity is defined as the number of trypsin units inhibited (TUI). The TUI per ml is calculated using the formula $$TUI\ [ml] = \frac{A_{blank} - A_{sample}}{0.01 \times V_{dl.smp.}}$$

where
$A_{blank}$=absorbance blank
$A_{sample}$=absorbance sample
$V_{dl.\ smp.}$=volume of the diluted sample solution in ml.

The thus obtained TUI is plotted against the volumes of the diluted sample solution, where the extrapolated value of the inhibitor volume to 0 ml gives the final TUI [ml]. Finally, the TUI per g sample is calculated with the formula $$TUI[g]=TUI[ml^{-1}] \times d \times 50$$

where d=dilution factor (final volume divided by the amount taken).

The results of this analytical method should not exceed 10% of the average value for repeated samples.

The enzyme urease catalyzes the degradation of urea to ammonia and carbon dioxide. Since urease naturally occurs in soybeans, the quantitative analysis of this enzyme is the most common test to evaluate the quality of processed soybeans. Preferably, the quantitative analysis of urease is done according to the method of ISO 5506 (1988) or AOCS Ba 9-58. The method of AOCS Ba 9-58 determines the residual activity of urease as an indirect indicator to assess whether the protease inhibitors have been destroyed in the processing of a feedstuff raw material and/or feedstuff. Said residual activity of urease is measured as increase in the pH value in the test as consequence of the release of the alkaline compound ammonia into the media. The recommended level for said increase of the pH value is 0.01 to 0.35 unit rise (NOPA, 1997). A typical quantitative analysis of the urease activity of a feedstuff raw material and/or feedstuff is done like this: First, a solution of urea in a buffer comprising $NaH_2PO_4$ and $KH_2PO_4$ is prepared, e.g. 30 g of urea are added to 1 l of a buffer solution composed of 4.45 g of $Na_2HPO_4$ and 3.4 g $KH_2PO_4$ and the pH value of the thus obtained is measured. Subsequently, a sample of a feedstuff raw material and/or feedstuff, e.g. 0.2 g of a soybean sample, is added to this solution. A test tube or beaker with the thus obtained solution, suspension, dispersion, or emulsion is placed in a water bath, e.g. at a temperature of 30+/−5° C., preferably 30° C., for 20 to 40 minutes, preferably 30 minutes. Finally, the pH value of this solution, suspension, dispersion, or emulsion is measured, compared with the pH value of the original urea solution, and the difference is given as increase in pH.

The solubility of proteins in alkali, hereinafter also referred to as the solubility of proteins in an alkaline solution or the alkali solubility of proteins, is an effective method to distinguish over-processed products from correctly-processed products, e.g. according to DIN EN ISO 14244.

The solubility of proteins in alkali or the alkali solubility of proteins comprises the determination of the percentage of protein that is solubilized in an alkali solution. Prior to the solubilization of the sample of a known weight of the feedstuff raw material and/or feedstuff, the nitrogen content of a sample with a specific weight is determined using a standard method for the determination of nitrogen, such as the Kjeldahl or Dumas method. The thus determined nitrogen content is referred to nitrogen content in total. Afterwards, a sample of the same weight and from the same source is suspended in an alkali solution of a defined concentration, preferably in an alkaline hydroxide solution, in particular in a potassium hydroxide solution. An aliquot of the thus obtained suspension is taken and centrifugated. Again, an aliquot of the thus obtained suspension is taken. The nitrogen content in this liquid fraction is determined using a standard method for the determination of nitrogen, such as the Kjeldahl or Dumas method. The thus determined nitrogen content is compared with the nitrogen content in total and expressed as the percentage of the original nitrogen content of the sample.

A typical alkali solution for the determination of the alkali solubility of proteins has a pH value of 12.5, for example, and a solution of potassium hydroxide with a concentration of 0.036 mol/l or 0.2% by weight. In step ii) 1.5 g of a soybean sample are for example placed in 75 ml of a potassium hydroxide solution, followed by stirring at 8500 rpm (rounds per minute) for 20 minutes at 20° C. Subsequently, an aliquot, for example about 50 ml, of the suspension, solution, dispersion or emulsion thus obtained are taken and immediately centrifugated at 2500 g for 15 min. Afterwards, an aliquot, for example 10 ml, of the supernatant of the suspension, solution, dispersion or emulsion thus obtained are taken and the content of nitrogen in said aliquot is determined by means of standard methods for the determination of nitrogen, such as the method of Kjeldahl or Dumas. Finally, the results are expressed as the percentage of the nitrogen content of the sample.

The determination of the protein dispersibility index (PDI) measures the solubility of proteins in water after blending a sample with water. This method also involves the determination of the nitrogen content in a sample of a known weight, which is typically done according to the same procedure as in the wet chemical analysis of proteins. The thus obtained nitrogen content is also referred to as the total nitrogen content. Further, the method also comprises the preparation of a suspension of a sample of the same weight as in the determination of the nitrogen content is suspended in water, which is typically done using a high-speed blender. The thus obtained suspension is filtered and the filtrate is subjected to a centrifugation. The nitrogen content in the thus obtained supernatant is determined by using again a standard method for the determination, such as the Kjeldahl or Dumas method, described above. The thus obtained nitrogen content is also referred to as the nitrogen content in solution. The protein dispersibility index is finally calculated as the ratio of the nitrogen content in solution to the total nitrogen content and expressed as the percentage of the original nitrogen content of the sample.

Since the values for the protein dispersibility index increases with decreasing particle size, the results obtained in the determination of the protein dispersibility index depend on the particle size of the sample. It is therefore preferred to grind the sample to be subjected to the determination of the protein dispersibility index, in particular with a 1 mm mesh size.

The procedure described above is in accordance with the Official Method Ba 10-65 of the American Oil Chemists' Society (A.O.C.S.), according to which the determination of the protein dispersibility index is preferably performed. The nitrogen content of for example a soy sample is determined by means of standard methods for the determination of nitrogen, such as the method of Kjeldahl or Dumas. An aliquot, for example 20 g, of the soy sample is placed in a blender, and (de-ionized) water, for example 300 ml, are added at 25° C., followed by stirring, for example at 8500 rpm for 10 minutes. The thus obtained suspension, solution, dispersion or emulsion is filtered and the thus obtained solution, dispersion or emulsion is centrifugated, e.g. at 1000 g for 10 minutes. Finally, the nitrogen content in the supernatant is determined by means of standard methods for the determination of nitrogen, such as the method of Kjeldahl or Dumas.

The set of reference data obtained from step a1) is used to find out data correlation with the cleaned spectra population of step b1) for generation of the prediction function in step c). In the case of the absolute or relative presence of one, several or all substance(s) in question in the sample, the data correlation refers to the concentration of the substance(s) in question in the sample.

In a preferred embodiment of the method according to the present invention the generation of the prediction function in step c) comprises analyzing the set of reference data of step a1) and the cleaned spectra population of step b7) for data correlation to give the prediction function.

The prediction quality achieved with the method according to the present invention can be improved by subjecting the prediction function generated in step c) to validation.

In a further embodiment of the method according to the present invention the generation of the prediction function in step c) comprises a validation of said prediction function.

In principle, the method according to the present invention is not subject to any limitation regarding the type of validation. Therefore, any suitable validation procedure can be used in the method according to the present invention. Notwithstanding, in the context of the present invention it is preferred to use a holdout cross validation, a k-fold validation and/or a validation against ring-test data. The latter option is a validation against external spectra and corresponding external reference data. This option has the advantages that the calibration population is not only evaluated with respect to its performance on the master spectrometer, i.e. the spectrometer used for the creation of the prediction function. Rather, this option also allows to evaluate the performance of the calibration population with respect to a network with a multitude of other spectrometers, for example hundreds of them, that also use the calibration function. Preference is therefore given to the use of a validation against ring-test data.

In a preferred embodiment of the method according to the present invention the validation is a holdout cross validation, a k-fold validation and/or a validation against ring-test data.

In the context of the present invention the terms holdout cross validation, k-fold validation and validation against ring-test data are used as known to the person skilled in the art.

For example, when the validation is a holdout cross validation, the step c) of the method according to the present invention further comprises the steps of cV1) portioning the reference data of step a1) and the cleaned spectra population of step b7) into a training set S0 and a test set S1, wherein the size of the test set S1 is smaller than the size of the training set S0, cV2) generating a preliminary prediction function on the training set S0 of step cV1), cV3) predicting a property value of interest by applying the preliminary prediction function of step cV2) on the cleaned spectra population, cV4) calculating the mean prediction error of the preliminary function of step cV2) with the predicted property values of step cV3) and the corresponding reference data of step cV1), cV5) repeating the steps cV1) to cV5), when the mean prediction error of the preliminary prediction function is outside a limit, or proceeding with step cV6), when the mean prediction error of the preliminary prediction function is within a limit, and cV6) approving the preliminary prediction function of step cV2) as prediction function.

For example, when the validation is a k-fold cross validation, the step c) of the method according to the present invention further comprises the steps of cV1) portioning the set of cleaned spectra population of step b7) and the corresponding reference data of step a1) into n subsets of equal size with n being an integer with a minimum of at least 2 and a maximum of less than the number of spectra, wherein one of the subsets is taken as test set and the remaining subsets are taken as training sets, cV2) generating a preliminary prediction function on a training set of step cV1), cV3) predicting a property value of interest by applying the preliminary prediction function of step cV2) on the cleaned spectra population, cV4) calculating the mean prediction error of the preliminary prediction function with the predicted property values of step cV3) and the corresponding reference data of step cV1), cV5) repeating the steps cV1) to cV5), when the mean prediction error of the preliminary prediction function is outside a limit, or proceeding with step cV6), when the mean prediction error of the preliminary prediction function is within a limit, cV6) approving the preliminary prediction function of step cV2) as prediction function and performing the steps cV2) to cV6) k-times with each of the n subsets used once as a test set to give k prediction functions, and cV7) averaging the parameters of each of the approved prediction functions of step cV6) to give a calibration function.

For example, when the validation is a validation against ring-test data, the step c) of the method according to the present invention further comprises the steps of cV1) providing a set of external reference spectra and corresponding reference data, cV2) generating a preliminary prediction function on the cleaned spectra population of step b7) and the reference data of step a1), cV3) predicting a property value of interest by applying the preliminary prediction function of step cV2) on the external reference spectra of step cV1), cV4) calculating the mean prediction error of the preliminary prediction function of step cV2) with the predicted property values of step cV3) and the corresponding external reference data of step cV1), cV5) repeating the steps cV1) to cV5), when the mean prediction error of the preliminary prediction function is outside a limit, or proceeding with step cV6), when the mean prediction error of the preliminary prediction function is within a limit, and cV6) approving the preliminary prediction function of step cV2) as prediction function.

Depending on the type of validation, the mean prediction error is also referred to as root mean square error of cross validation (RMSECV), when the validation is an internal validation, in particular a cross-validation, and is calculated by means of the formula $$RMSECV = \sqrt{\frac{1}{M}\sum_{i=1}^{M}(y_i^{measured} - y_i^{predicted})^2}$$

wherein M=number of the predicted property values,
$y_i^{measured}$=measured property value,
$y_i^{predicted}$=predicted property value.

In general, validating the prediction function obtained by the method according to the present invention or in any of its embodiments already gives a very reliable and useful prediction function. Notwithstanding, in rare cases it may be suitable to further evaluate the prediction function generated in the method according to the present invention or in any of its embodiments. A useful approach is to plot, the property values predicted for the cleaned spectra population of step b7), and the prediction function of step c) as a regression line into a measured-vs-predicted plot to give a scatter plot. Optionally, the property values of the reference data of step a1) are also plotted into said plot. Then, an angle bisector is plotted into the thus obtained scatter plot to divide the plane of said plot into two triangular planes of equal size. In theory, the plotted prediction function and the angle bisector would be congruent, if the prediction function was perfect. However, in practice this is rarely the case. Next, the distances of each predicted property value to the angle bisector in the scatter plot are determined, and an overall ranking of said distances is formed, with the highest distances at the top of the ranking. The spectra corresponding to the at least three top ranked distances, i.e. predicted property values, are removed from the cleaned spectra population of step b7). Then the prediction function of step c) is revised for compensating the removal of the spectra. This approach permits for a further fine tuning of the prediction function. The result of this fine tuning can be easily followed when the approach is stepwise repeated: each repetition moves the prediction function closer to the angle bisector.

In another preferred embodiment of the method according to the present invention the step c) further comprises the steps of c1) plotting the property values predicted for the cleaned spectra population of step b7), and the prediction function of step c) as a regression line into a measured-vs-predicted plot to give a scatter plot, c2) plotting an angle bisector between the axes of the plot of step c1), c3) determining the distances of each predicted property value of step c1) to the angle bisector in the scatter plot of step c2), c4) forming an overall ranking of the distances obtained in step c3), with the highest distances at the top of the ranking, and removing the spectra corresponding to the at least three top ranked distances from the cleaned spectra population of step b7), and c5) revising the prediction function of the step c) for compensating the removal of spectra in step c4).

In the context of the present invention the term revising the prediction function is used to denote the generation of a new prediction function on the cleaned spectra population resulting from the additional removal of spectra in step c4) above.

It may be that in some cases two or more spectra corresponding to top ranked distances, which are to be removed from the cleaned spectra population of step b7), are in (tight) neighborhood in the scatter plot. However, the removal of two or more spectra in (tight) neighborhood can excessively influence the slope of the revised prediction function. In the worst case the slope of the prediction function is substantially affected, e.g. revising the prediction function leads to a higher or lower slope than before.

This effect can be avoided or at least significantly reduced by a weighting of the two or more spectra corresponding to top ranked distances, which are to be removed from the cleaned spectra population of step b7), when they are in (tight) neighborhood in the scatter plot. For this purpose, first, a vertical line is plotted through the angle bisector at the half length of said angle bisector, so that the planes above and below the angle bisector are divided into two planes each, wherein the respective planes mirrored at the angle bisector are of equal size. Generally, four planes are formed by dividing the plane between the axes of the scatter plot with the angel bisector and the vertical line plotted through the angle bisector at the half of its length: two triangles of equal size and two squares of equal size, with each one triangle and one square above and below the angle bisector. Next, the two or more spectra corresponding to top ranked distances, which are to be removed from the cleaned spectra population of step b7), are weighted by a factor of 0.5, when they are present in the same plane given by the angle bisector and the vertical line.

In another preferred embodiment the process according to the present invention therefore further comprises that in step c2) a vertical line is plotted through the angle bisector at the half length of said angle bisector, to divide the plane between the axes of the scatter plot into four planes, and in step c4) the spectra corresponding to at least two top-ranked distances are weighted by a factor of 0.5, when they are present in the same plane.

In principle, the approach described above can be performed until the prediction function and the angle bisector are congruent. In practice, one would repeat the procedure of steps c1) to c5) until there is no further improvement in convergence of the prediction function to the angle bisector, or in other words until the plot of the thus obtained revised prediction function as a regression line is as close as possible to the angle bisector.

In a further preferred embodiment the process according to the present invention further comprises the step of c6) repeating the steps c1) to c5) with the revised prediction function and the cleaned spectra population obtained from a preceding revision until the plot of the thus obtained revised prediction function as a regression line is as close as possible to the angle bisector.

As an alternative or in addition to the procedure of steps c1) to c5) with or without c6), it is also possible to further improve the quality of the prediction function of step c) by means of a confidence interval. This, first, comprises plotting the plotting the property values predicted for the cleaned spectra population of step b7), and the prediction function of step c) as a regression line into a measured-vs-predicted plot to give a scatter plot. Next, like in the procedure described above, an angle bisector is plotted between the two axes of the scatter plot, and a confidence interval with a predetermined width is plotted around the angle bisector. Subsequently, the spectra corresponding to the spots outside the confidence interval are removed from the cleaned spectra population of step b7) and the prediction function of step c) is subjected to a revision for compensating the removal of the spectra. In the context of the present invention the confidence interval has a width from +5×RMSECV to −5×RMSECV, preferably from +4×RMSECV to −4×RMSECV, +3×RMSECV to −3×RMSECV, +2×RMSECV to −2×RMSECV, +1×RMSECV to −1×RMSECV or a width from any positive real number to the corresponding negative real number between +5×RMSECV and −5×RMSECV, around the respective value of the angel bisector, wherein the RMSECV is the root mean square error of cross validation as defined above.

In a further embodiment the method according to the present invention further comprises the steps of c7) plotting the property values predicted for the cleaned spectra population of step b7), and the prediction function of step c) as a regression line into a measured-vs-predicted plot to give a scatter plot, c8) plotting an angle bisector between the two axes of the plot of step c7), c9) plotting a confidence interval with a predetermined width around the angle bisector into the plot of step c8), c10) removing the spectra corresponding to the spots outside the confidence interval in the plot of step c9) from the cleaned spectra population of step b7), and c11) revising the prediction function of the step c) for compensating the removal of spectra in step c10).

In the context of the present invention the term revising the prediction function is used to denote the generation of a new prediction function on the cleaned spectra population resulting from the additional removal of spectra in step c10) above.

Again, it may be that in some cases two or more spectra corresponding to top ranked distances, which are to be removed from the cleaned spectra population of step b7), are in (tight) neighborhood in the scatter plot. However, the removal of two or more spectra in (tight) neighborhood can excessively influence the slope of the revised prediction function. In the worst case the slope of the prediction function is substantially affected, e.g. revising the prediction function leads to a higher or lower slope than before.

This effect can be avoided or at least significantly reduced by a weighting of the two or more spectra corresponding to top ranked distances, which are to be removed from the cleaned spectra population of step b7), when they are in (tight) neighborhood in the scatter plot. For this purpose, first, a vertical line is plotted through the angle bisector at the half length of said angle bisector, so that the planes above and below the angle bisector are divided into two planes each, wherein the respective planes mirrored at the angle bisector are of equal size. Generally, four planes are formed by dividing the plane between the axes of the scatter plot with the angel bisector and the vertical line plotted through the angle bisector at the half of its length: two triangles of equal size and two squares of equal size, with each one triangle and one square above and below the angle bisector. Next, the two or more spectra corresponding to top ranked distances, which are to be removed from the cleaned spectra population of step b7), are weighted by a factor of 0.5, when they are present in the same plane given by the angle bisector and the vertical line.

In another preferred embodiment the process according to the present invention therefore further comprises that in step c8) a vertical line is plotted through the angle bisector at the half length of said angle bisector, to divide the plane between the axes of the scatter plot into four planes, and in step c10) the spectra corresponding to at least two top-ranked distances are weighted by a factor of 0.5, when they are present in the same plane.

In principle, the approach described above can be performed until the prediction function and the angle bisector are congruent. In practice, one would repeat the procedure of steps c7) to c11) until there is no further improvement in convergence of the prediction function to the angle bisector, or in other words until the plot of the thus obtained revised prediction function as a regression line is as close as possible to the angle bisector.

In a further preferred embodiment the process according to the present invention further comprises the steps of c12) repeating the steps c7) to c11) with the revised prediction function and the cleaned spectra population obtained from a preceding revision until the plot of the thus obtained revised prediction function as a regression line is as close as possible to the angle bisector.

It may be beneficial to subject the spectra of step a) to a data preprocessing in order to facilitate the subsequent analysis of the spectra.

In another embodiment the method according to the present invention further comprises, prior to step b), the step of a3) subjecting the infrared spectra of step a) to a data preprocessing, wherein said data preprocessing is one or more selected from the group consisting of smoothing, multiplicative scatter correction, standard normal variate transformation, detrending, taking a derivative of a spectrum, and continuous piecewise direct standardization.

Inherent in the collection of spectra taken over time is some form of random variation or noise. The so-called smoothing is a suitable method for removing noise and better exposing the signal of the underlying causal processes. In the context of the present invention smoothing is preferably a moving average smoothing, a polynomial smoothing with a Savitzky-Golar filter and/or an extended signal to noise ratio polynomial smoothing.

Calculating a moving average involves creating a new series where the values are comprised of the average of raw observations in the original time series. A moving average requires to specify a window size called the window width. This defines the number of raw observations used to calculate the moving average value. The "moving" part in the moving average refers to the fact that the window defined by the window width is slid along the time series to calculate the average values in the new series.

A Savitzky-Golay filter is a digital filter that can be applied to a set of digital data points for the purpose of smoothing the data, that is, to increase the precision of the data without distorting the signal tendency. This is achieved, in a process known as convolution, by fitting successive sub-sets of adjacent data points with a low-degree polynomial by the method of linear least squares. When the data points are equally spaced, an analytical solution to the least-squares equations can be found, in the form of a single set of "convolution coefficients" that can be applied to all data sub-sets, to give estimates of the smoothed signal, (or derivatives of the smoothed signal) at the central point of each sub-set.

Detrending is a type of baseline correction; it is performed through subtraction of a linear or polynomial fit of the baseline from the original spectrum to remove tilted baseline variation, usually found in NIR reflectance spectra of powdered samples.

Standard normal variate (SNV) is another frequently used pre-treatment method due to its simple algorithm and effectiveness in scattering correction. It is often used on spectra where baseline and pathlength changes cause differences between otherwise identical spectra.

Multiplicative scatter correction (MSC) is performed by regressing a measured spectrum against a reference spectrum and then correcting the measured spectrum using the slope and intercept of this linear fit. This pretreatment method has proven to be effective in minimizing baseline offsets and multiplicative effects. The outcome of MSC, in many cases, is very similar to SNV. Nevertheless, many spectroscopist prefer SNV over MSC since SNV corrects each spectrum individually and does not need the entire data set. The extended multiplicative signal correction preprocessing method allows for a separation of physical light-scattering effects from chemical absorbance effects in spectra from powders or turbid solutions, for example. The model-based method is particularly useful in minimizing wavelength-dependent light scattering variation. After pretreatment the corrected spectra become insensitive to light scattering variations and respond linearly to the analyte concentration.

Cases may arise, where the position of a signal peak in a spectrum cannot be located because the maxima and minima of the individual peaks cannot be clearly identified due an overlap for example. An easier locating of individual peaks in the spectrum is possible, when the minima and maxima of the peaks are easier identifiable. Taking the first derivative of a spectrum facilitates the identification of the peaks in the spectrum because it gives a zero crossing of peak maxima or peak minima. Taking the second derivative gives a peak minimum at exactly that position, where a peak maximum was in the original spectrum and vice versa. Taking the first or second derivative of a spectrum also facilitates the identification of an outlier in the population of spectra of known feedstuff raw materials and/or feedstuffs. In the context of the present invention it is therefore preferred to take the first and/or second derivative of a spectrum.

Continuous piecewise direct standardization (CPDS) is used to account for the variation in the spectra resulting from continuous external factors, such as temperature. The first step in the PDS and CPDS algorithms is to construct a PLS model between the spectra, $X(t_{ref})$ which is the order of m×n, and the response matrix, Y, for a specific temperature $t_{ref}$. According to the piecewise direct standardization (PDS) algorithm, a matrix is then calculated that transforms the spectral measurements recorded at temperature values other than at $t_{ref}$:

$$X(t_{ref})=X(t_k)\times Q(t_k), (k=1,2,\ldots,k;t_k\neq t_{ref})$$

where $Q(t_k)$ is a m×m banded transformation matrix that is obtained by linearly regressing the j-th column of $X(t_{ref})$ on a sub-matrix taken from $X(t_k)$ (i.e. the spectra in $X(t_k)$ corresponding to a window of wavelengths from j−w to j+k), using PLS, where the window size, 2w+1, is determined by the tuning parameter w. $Q(t_k)$ is then formed by placing the regression vectors on corresponding blocks. This procedure is repeated for each temperature value $t_k$, (k=1, 2, . . . , k; $t_k\neq t_{ref}$), and K transformation matrices are obtained by noting that $Q(t_k)$ is an identity matrix. To account for the effect of continuous temperature values, a polynomial function is fitted against the temperature difference $\Delta t_k$, where $\Delta t_k=t_k-t_{ref}$, to the non-zero elements of the banded matrix $Q(t_k)$:

$$q_{ij}(t_k)=a_{ij}+b_{ij}\Delta t_k+c_{ij}\Delta t_k^2+e_{ij}$$

where $q_{ij}(t_k)$ is the element of $Q(t_k)$ for the i-th row and the j-th column. Once the parameters of the polynomial function have been estimated, the transformation matrix for the spectra measured at an unseen temperature value, $t_{test}$, in the test stage can be calculated by applying the formula above for $q_{ij}(t_k)$. Hence, the temperature influence can be removed by transforming the spectral matrix as if were measured at the reference temperature:

$$X(t_{ref}|t_{test})=X(t_{test})\times Q(t_{test})$$

The responses can then be predicted by the PLS model built under the reference temperature.

Preferably, the infrared spectra of step a) are subjected to a standard normal variate transformation, detrending and taking the first derivative of a spectrum, preferably, in the given order.

It not only facilitates but more importantly also improves the prediction quality of the prediction function generated by the method according to the present invention when only the signals, which are at equidistant wavelengths from one another in a spectrum, are considered. This approach significantly reduces the danger of losing any relevant signals and information in a spectrum. This is in particular relevant with respect to concentration series of complex mixtures with more than just one infrared active component, where the signal intensities significantly increases with the concentration of each component. Hence, the signals of a component with low concentration in said complex mixture may be (partially) superimposed by the signals of another component with higher concentration. In this case, the neglection or loss of just a single signal in a spectrum may already result in an erroneous data correlation and/or the generation of an erroneous prediction function and thus, wrong prediction results.

Therefore, in a further embodiment of the method according to the present invention the signals with equidistant wavelength distances from one another in a spectrum are considered in step b) and/or c).

In cases where a data preprocessing leads to differences in the wavelengths scale of a spectrum before and after data preprocessing, it is beneficial to correct the spectrum as a whole. This is in particular relevant regarding the correct position of wavelengths of extreme points, i.e. signals with relative maximum or minimum of absorption. It is therefore preferred to subject a spectrum with non-equidistant wavelength distances to a type of correction in order to get the correct spectrum with equidistant wavelength distances. The correct wavelengths of the extreme points, i.e. the points of a relative maximum of absorptions and relative minima of absorptions, are a good basis for correcting a spectrum as a whole. First, the position of the extreme points in one or more spectra is moved from the shifted, i.e. not correct, wavelengths to the corrected wavelengths, where the respective signals are expected to be. For example, specific signals of functional groups in a compound are known to be found at specific wavelengths in an infrared spectrum. In the next step, a graph is drawn through the extreme points at the corrected wavelengths and where appropriate, though the other points of the spectrum, whose positions are not affected by the wavelengths shifts. This can be done by means of interpolation. However, it may be difficult or even not really practicable to draw only one single graph through all extreme points in a spectrum to be corrected. Rather, better results are achieved when several polynomials are used for connecting adjacent points in a spectrum to be corrected, because they smoothly combine to one single graph. This can be done by (cubic) spline interpolation. The (cubic) spline interpolation can be visualized as a flexible strip that is bent to pass through each of the extreme points in the spectrum whose graphical representation is to be interpolated. From a mathematical point of view, this strip can be described by a series of cubic polynomials, which must meet the requirements that i) the thus obtained spline has to go through all function values, when one considers the graphical representation of a spectrum as a function, or a section-wise defined function, ii) the first and second derivatives of the cubic polynomials are continuous, and iii) the curvature is forced to zero at the endpoints of the interval in the spectrum. Once the corrected wavelengths of the extreme points are known, the cubic polynomials can easily be calculated by means of any suitable commercially available mathematical program. Low requirements on computing capacity are therefore a further advantage of (cubic) spline interpolation. Hence, spline interpolation or cubic spline interpolation is very useful for interpolating data in a spectrum to new wavelengths and for generating continua in the corrected spectrum.

In yet another embodiment the method according to the present invention further comprises, prior to step b), the step of a3) subjecting a spectrum with non-equidistant wavelength distances to a cubic spline interpolation to provide a spectrum with equidistant wavelength distances.

Preferably, the step a3) is performed after step a2) and prior to step b).

The method according to the present invention is not subject to any limitation regarding the number of prediction functions to be generated. If a specific number of different populations of spectra are provided in step a), the corresponding number of prediction functions for each population will be generated. Alternatively, if the population of infrared spectra of step a) comprises infrared spectra of different classes of samples, the method according to the present invention will generate the corresponding prediction function for each of these classes of samples.

In the method according to the present invention an infrared spectrum of a sample of unknown origin and/or composition or of the same origin and/or composition as a sample in step a) is provided in step d) and then, a property value of interest is predicted from said spectrum by means of the prediction function of step c) for the sample of the spectrum of step d). For this purpose, it needs the selection of the suitable prediction function which fits to the sample spectrum in question. In principle, the prediction function could be selected on the information available for the sample whose infrared spectrum is provided in step d), for example the information given on a bag of feed, feedstuff etc. However, this information could be incorrect and thus lead to the selection of the wrong prediction function, or the user of the method could select a prediction function at his own discretion, which however may be the wrong prediction function with respect to the sample spectrum in question.

It is therefore preferred, that the method according to the present invention selects the prediction function which fits most adequately to the infrared spectrum of the sample in question. A suitable approach is to identify the similarity between the sample spectrum provided in step d) and any of the cleaned spectra population of step b7) or the centroid of said cleaned spectra population. The first step of this approach includes transforming the absorption intensities of wavelengths or wavenumbers in the spectrum of step d) to a query vector and to compare this query vector with a database vector obtained from transforming the absorption intensities of wavelengths or wavenumbers in the cleaned spectra population of step b7) to a set of database vectors or from transforming the absorption intensities of wavelengths or wavenumbers of the centroid of the cleaned spectra population of step b7) to a database vector. It is preferred to compare the query vector with each database vector of the set of database vectors. In its broadest meaning a vector is a geometric object that has magnitude (or length) and direction. In a Cartesian coordinate system, a vector can be represented by identifying the coordinates of its initial and terminal point. Therefore, a vector is suited to represent an absorption intensity at a specific wavelength or wavenumber in a two-dimensional near infrared spectrum. In addition, a vector is not limited to the description of a two-dimensional system. Rather, a vector can describe multi-dimensional spaces, such as a near infrared spectrum with a multitude of absorption intensities at a multitude of different wavelengths or wavenumbers. In this case, each dimension of the said vector corresponds to a single absorption intensity at a specific wavelength or wavenumber. Next step is the calculation of a similarity measure and/or a distance measure between the query vector and a database vector or each vector of a set of database vectors and ranking the thus obtained similarity measure and/or a distance measure with the best values at the top of the ranking, i.e. the similarity measure with the highest value at the top or the distance measure with the lowest value at the top. The prediction function corresponding to a cleaned spectra population from which a database vector has the highest similarity in step d4) is then selected for the prediction in step e).

Preferably, the step d) of the method according to the present invention therefore further comprises the steps of
d1) transforming absorption intensities of wavelengths or wavenumbers in the spectrum of step d) to a query vector,
d2) transforming the absorption intensities of wavelengths or wavenumbers in the cleaned spectra population of step b7) to a set of database vectors or transforming the absorption intensities of wavelengths or wavenumbers of the centroid of the cleaned spectra population of step b7) to a database vector,
d3) calculating a similarity measure and/or a distance measure between the query vector of step d1) and a database vector of step d2) to give a similarity value for the query vector with the database vector,
d4) ranking the similarity values obtained in step d3) in descending order, when a similarity measure is calculated in step d3) or in ascending order, when a distance measure is calculated in step d3), wherein in any case the top-ranked database vector has the highest similarity with the query vector, and
d5) selecting the prediction function corresponding to a cleaned spectra population from which a database vector has the highest similarity in step d4) for the prediction in step e).

It is preferred to transform absorption intensities at equidistant wavelengths or wavenumbers in the spectrum of step d) and in cleaned spectra population of step b7) and in particular at the same equidistant wavelengths or wavenumbers in the spectrum of step d) and in the cleaned spectra population of step b7) to a vector. This allows for the best possible similarity analysis. Preferably, the distance between the wavelengths in step d1) and/or d2) of the method according to the present invention is from 0.1+/−10% to 10+/−10% nm, from 0.1+/−10% to 5+/−10% nm, or from 0.1+/−10% to 2+/−10% nm. Accordingly, the distance between the wavenumbers in step d1) and/or d2) of the method according to the present invention is from 108+/−10% to 106 10+/−10%, from 108+/−10 to 5*106+/−10% nm, or from 108+/−10% to 2*106+/−10% nm. In the context of the present invention, the term +/−10% is used with respect to explicitly mentioned values to indicate that deviations from said explicitly mentioned values are still within the scope of the present invention, provided that they essentially lead to the effects of the present invention.

The similarity analysis in step d3) is not subject to any limitations regarding the use of a specific distance or similarity measure. In principle, a similarity analysis is a search for the nearest neighbor. Hence, any similarity measure suitable for determining the nearest neighbor to the query vector can be used in in step d3).

The cosine similarity is an example of a similarity measure suitable for use in the context of the present invention. It allows for the calculation of the similarity between two vectors extremely quickly and at the same time with a high precision. The cosine similarity $C_{A,B}$ between two observations, i.e. two vectors of spectra, can be calculated by means of the formula $$C_{A,B} = \frac{\sum_{i=1}^{n} A_i B_i}{\sqrt{\sum_{i=1}^{n} A_i^2} \sqrt{\sum_{i=1}^{n} B_i^2}}$$

wherein $A_i$ and $B_i$ are components of the vectors A and B, of which one vector is the query vector and the other vector is a database vector, and n is the number of considered vectors. The values for a similarity measure can range from −1 meaning exactly the opposite to each other, via 0, indicating orthogonality (decorrelation) to +1, meaning identity, with in-between values indicating intermediate similarity or dissimilarity.

The Euclidian distance is an example of a distance measure suitable for use in the context of the present invention. It allows for the calculation of the dissimilarity between two vectors extremely quickly and at the same time with a high precision. If desired, the thus obtained distance measure can be easily calculated into a similarity measure for use in the method according to the present invention. The Euclidian distance $E_{A,B}$ between two observations, i.e. two vectors of spectra, can be calculated by means of the formula $$E_{A,B} = \sqrt{\sum_{i=1}^{n} (A_i^2 - B_i^2)^2}$$

wherein $A_i$ and $B_i$ are components of the vectors A and B, of which one vector is the query vector and the other vector is a database vector, and n is the number of considered vectors. The values for a distance measure can range from +1 meaning exactly the opposite to each other, via 0, indicating orthogonality (decorrelation) to −1, meaning identity, with in-between values indicating intermediate similarity or dissimilarity.

Another object of the present invention is a system for predicting a property value of interest of a material, comprising a processing unit, adapted to carry out the computer-implemented method for predicting a property value of interest of a material according to the present invention and/or any embodiments thereof.

The one or more prediction functions generated in the method according to the present invent is/are stored in the processing unit of the system. The allows for a communication between the system according to the present invention and one or more infrared spectrometers at the same location as said system and/or at a different location.

In an embodiment of the system according to the present invention the processing unit forms a network with one or more infrared spectrometers.

The invention claimed is:

1. A computer-implemented method for predicting a property value of interest of a material, the method comprising:
   a) providing a population of infrared spectra of samples, wherein the spectra form an m×n input data matrix X, with m being the number of samples in rows and n being the data points in columns,
   b) removing spectral outliers from the spectra population of step a), the removing comprising:
      b1) obtaining the principal components by subjecting the matrix X to a principal component analysis,
      b2) producing a diagonal matrix Σ, comprising singular values $\sigma_m$ of the matrix X, and a loadings matrix V, from the input data matrix X,
      b3) calculating a score $x_m$ for each spectrum by multiplying each data point of the input data matrix X with the loadings for each component of step b2), forming the mean of each column of the X-matrix to provide $B_{0,m}$ values, and calculating a scoring index si by the formula $$si = \sum_i \frac{(x_m - B_{0,m})}{\sigma_m}$$

b4) determining the number of components $N_C$ whose eigenvalues lead to a convergence in the regression of X on the scores of at least 99%, and calculating a distance measure threshold value $D_i$ for every spectrum of step a), by the formula $$D_i = N_C \times \sqrt[2]{\frac{(si^2 \times N_C)}{(N_C - 1)}}$$

b5) calculating the mean for all scores of each principal component of each spectrum of step a) and calculating the distance measure between the mean and each of the scores of each principal component,
   b6) considering a sample spectrum as a spectral outlier when the value of the distance measure for a score of a principal component obtained in step b5) is larger than the distance measure threshold value of step b4),
   b7) removing the spectral outlier of step b6) from the spectra population of step a) to give a cleaned spectra population,
   c) generating a prediction function on the cleaned spectra population of step b7),
   d) providing an infrared spectrum of a sample of unknown origin and/or composition or of the same origin and/or composition as a sample in step a), and
   e) predicting a property value of interest from the spectrum of step d) by means of the prediction function of step c).

2. The method according to claim 1, wherein the distance measure is the Euclidian distance measure, the Pearson distance measure, the Mahalanobis distance measure, or a distance measure obtained from a similarity measure.

3. The method according to claim 1, wherein the step b) further comprises:
   b5.1) increasing the distance measure threshold value obtained in step b4) by +1,
   b5.2) determining the two distance measures obtained in step b5) with the highest values using the distance measure threshold value of step b5.1),
   b5.3) determining the difference between the values of the distances measures determined in step b5.2), and
   b5.4) repeating the steps d5.1) to d5.3) with the distance measure threshold value of step b5.1) until the difference determined in step b5.3) is at least 1, and the highest value of a distance measure is 8 at the most.

4. The method according to claim 1, further comprising:
   a1) determining the property values of interest in each sample of step a) in a quantitative analysis to give a set of reference data.

5. The method according to claim 4, wherein the generation of the prediction function in step c) comprises analyzing the set of reference data of step a1) and the cleaned spectra population of step b7) for data correlation to give the prediction function.

6. The method according to claim 5, wherein the step c) further comprises:
   c1) plotting the property values predicted for the cleaned spectra population of step b7), and the prediction function of step c) as a regression line into a measured-vs-predicted plot to give a scatter plot,
   c2) plotting an angle bisector between the axes of the plot of step c1),
   c3) determining the distances of each predicted property value of step c1) to the angle bisector in the scatter plot of step c2),
   c4) forming an overall ranking of the distances obtained in step c3), with the highest distances at the top of the ranking, and removing the spectra corresponding to the at least three top ranked distances from the cleaned spectra population of step b7), and
   c5) revising the prediction function of the step c) for compensating the removal of spectra in step c4).

7. The method according to claim 6, further comprising:
   c6) repeating the steps c1) to c5) with the revised prediction function and the cleaned spectra population obtained from a preceding revision until the plot of the thus obtained revised prediction function as a regression line is as close as possible to the angle bisector.

8. The method according to claim 5, further comprising:
   c7) plotting the property values predicted for the cleaned spectra population of step b7), and the prediction function of step c) as a regression line into a measured-vs-predicted plot to give a scatter plot,
   c8) plotting an angle bisector between the two axes of the plot of step c7),
   c9) plotting a confidence interval with a predetermined width around the angle bisector into the plot of step c8),
   c10) removing the spectra corresponding to the spots outside the confidence interval in the plot of step c9) from the cleaned spectra population of step b7), and
   c11) revising the prediction function of the step c) for compensating the removal of spectra in step c10).

9. The method according to claim 8, further comprising:
   c12) repeating the steps c7) to c11) with the revised prediction function and the cleaned spectra population obtained from a preceding revision until the plot of the thus obtained revised prediction function as a regression line is as close as possible to the angle bisector.

10. The method according to claim 1, wherein the generation of the prediction function in step c) comprises a validation of the prediction function.

11. The method according to claim 10, wherein the validation is at least one selected from the group consisting of a holdout cross validation, a k-fold validation, and a validation against ring-test data.

12. The method according to claim 1, further comprising, prior to step b):
   a2) subjecting the infrared spectra of step a) to a data preprocessing, wherein the data preprocessing is one or more selected from the group consisting of smoothing, multiplicative scatter correction, standard normal variate transformation, detrending, taking a derivative of a spectrum, and continuous piecewise direct standardization.

13. The method according to claim 1, further comprising, prior to step b):
   a3) subjecting a spectrum with non-equidistant wavelength distances to a cubic spline interpolation to provide a spectrum with equidistant wavelength distances.

14. A system for predicting a property value of interest of a material, the system comprising:
   a processing unit, adapted to carry out the computer-implemented method for predicting a property value of interest of a material according to claim 1.

15. The system according to claim 14, wherein the processing unit forms a network with one or more infrared spectrometers.

\* \* \* \* \*